United States Patent [19]

Fasching

[11] Patent Number: 4,926,112

[45] Date of Patent: May 15, 1990

[54] 3-D CAPACITANCE DENSITY IMAGING OF FLUIDIZED BED

[76] Inventor: George E. Fasching, 653 Vista Pl., Morgantown, W. Va. 26505

[21] Appl. No.: 170,229

[22] Filed: Mar. 18, 1988

[51] Int. Cl.[5] .............................................. G01R 27/26
[52] U.S. Cl. .................................... 324/664; 324/690; 73/61 R; 73/61.1 R
[58] Field of Search .......................... 324/61 R, 61 P; 73/61 R, 61.1 R

[56] References Cited

U.S. PATENT DOCUMENTS

| | | | |
|---|---|---|---|
| 3,221,248 | 11/1965 | Batteau et al. | 324/61 R |
| 3,639,835 | 2/1972 | Dammig, Jr. et al. | 324/61 R |
| 3,903,478 | 9/1975 | Stewart et al. | 324/61 R |
| 4,493,039 | 1/1985 | Gregory | 324/61 R |
| 4,689,986 | 9/1987 | Garson et al. | 73/61 R |
| 4,689,988 | 9/1987 | Rydefalk | 73/61 R |

OTHER PUBLICATIONS

The Use of Capacitance Probes in Fluidized Beds, Power Technology, 1972, pp. 45–50, D. Geldart, J. R. Kelsey.

Primary Examiner—Reinhard J. Eisenzopf
Assistant Examiner—Maura K. Regan

[57] ABSTRACT

A three-dimensional capacitance density imaging of a gasified bed or the like in a containment vessel is achieved using a plurality of electrodes provided circumferentially about the bed in levels and along the bed in channels. The electrodes are individually and selectively excited electrically at each level to produce a plurality of current flux field patterns generated in the bed at each level. The current flux field patterns are suitably sensed and a density pattern of the bed at each level determined. By combining the determined density patterns at each level, a three-dimensional density image of the bed is achieved.

13 Claims, 6 Drawing Sheets

VOID LOCATIONS

3-D CAPACITANCE DENSITY IMAGING OF FLUIDIZED BED

FIELD OF THE INVENTION

The present invention relates generally to the monitoring of fluidized beds, and more particularly to a three-dimensional capacitance density imaging of a fluidized bed.

BACKGROUND OF THE INVENTION

Knowledge of the void fraction within the bed of a fluidized-bed combustor or gasifier is vital to the design and operation of such units. Predictive modeling of fluidized-bed performance is also highly dependent upon a broad data base of dynamic void fraction information for various bed geometries, size, and bed conditions.

A two-dimension and three-dimension density imaging system in wide spread utilization today is the computerized axial tomography system. The systems are typically used in medical and industrial applications. However, these nuclear-based scanning systems are very bulky, massive, and expensive. Furthermore, the systems scan at a slow rate due to the mechanical scan method employed and the nuclear event counting time required. Such a system would not be suitable to study dynamic fluidized-bed behavior, where rapid three-dimension mapping of a bed density field is required. In some applications, mapping rates of one hundred times per second will be necessary.

SUMMARY OF THE INVENTION

The present invention is an apparatus and method for providing a three-dimensional capacitance density imaging of a gasified bed or the like in a containment vessel. This imaging is accomplished by providing a plurality of electrodes circumferentially about the bed in levels and along the bed in channels. These electrodes are then individually and selectively excited by a suitable excitation means at each level whereby a plurality of current flux field patterns are generated in the bed at each level. These current flux patterns at each level are sensed by a suitable sensing means and a determining means then determines a density pattern of the bed at each level from the sensed current flux patterns. Finally, the determined density patterns are combined at each level to provide a three-dimensional density image of the bed.

In a preferred embodiment, the electrodes are excited by either a positive 0°-phase voltage, a negative 180°-phase voltage, or a zero voltage. Both symmetrical and non-symmetrical current field patterns can be produced. The excitation means preferably includes an excitation transformer for each electrode channel. The excitation transformer includes a shielded multi-turn secondary winding for each electrode in the associated channel.

In the preferred embodiment, the excitation means includes a means for maintaining the electrical excitation at a predetermined voltage. In addition, the electrodes in each channel include a sense electrode at each level and guard electrodes at each end of the channel which are connected to the secondary winding shields. A clock means is further provided for generating a reference signal for the excitation means, sensing means, and determining means. Further, the sensing means includes a switch means for allowing the sensing of capacitance current at any two different electrode combinations of the selected level.

It is a feature of the present invention that the imaging system provides three-dimensional density images or maps at a rate of about 100 maps per second with a resolution of one inch or better, depending on bed size, shape, and operating conditions. This speed of mapping is achieved using electronic switching.

It is also a feature of the present invention that the electrodes required for the measurements are mounted flush with the inside surface of the bed containment vessel rendering these electrodes essentially non-intrusive.

It is an advantage of the present invention that the monitoring system can be used for monitoring fluidized-bed operation for the purpose of characterizing bed voidages, solids/gas behavior, operating regime identification, bed height, and bed activity. Further, the sensing system is also usable for sensing voidage patterns in solid flow systems and reactors for improved operability.

Other features and advantages of the present invention are stated in or apparent from a detailed description of a presently preferred embodiment of the invention found hereinbelow.

DETAILED DESCRIPTION OF THE PEFERRED EMBODIMENTS

Figure 1A:
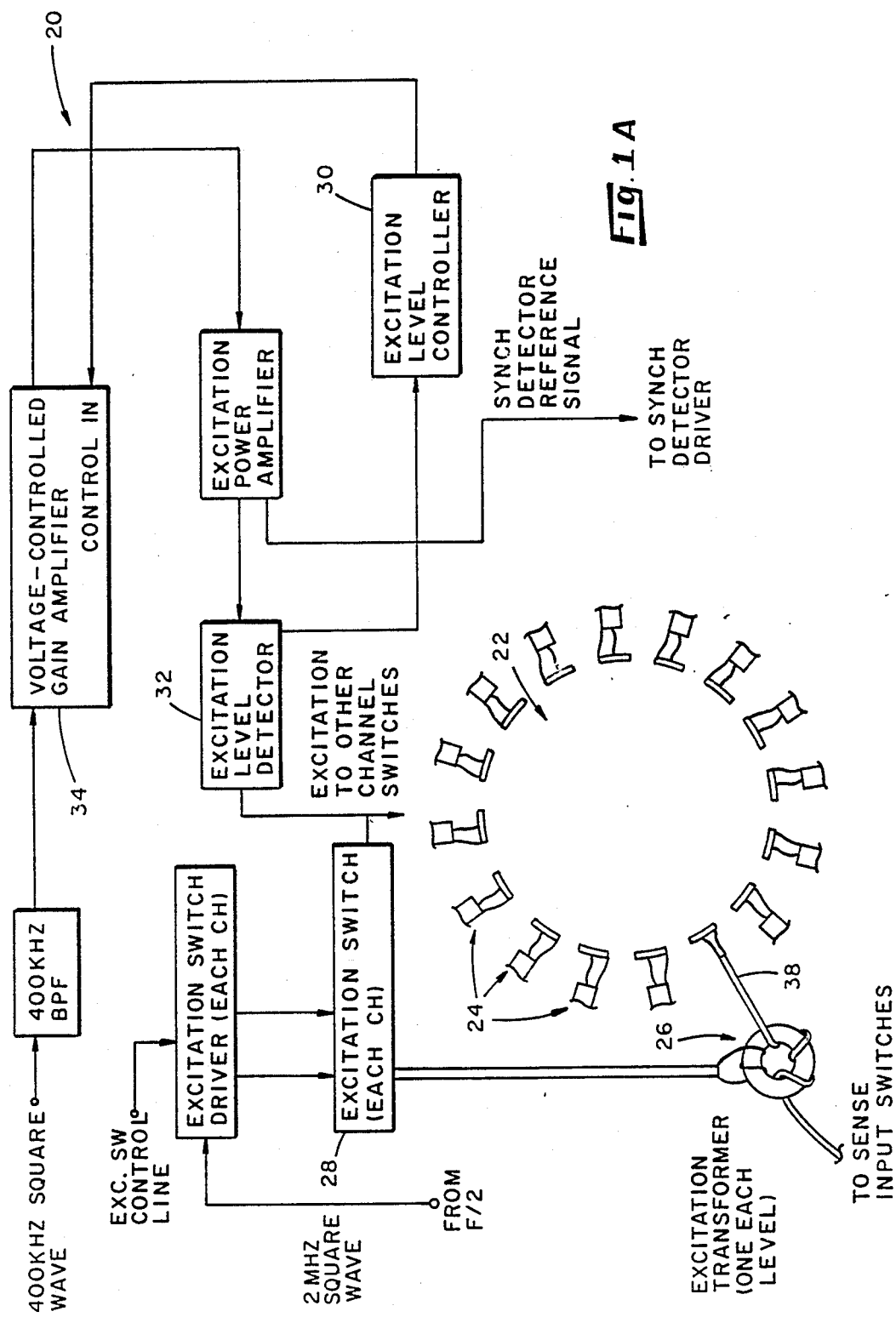
FIGS. 1A and 1B are associated halves of a schematic block diagram of the capacitance imaging system of the present invention.
Figure 1B:
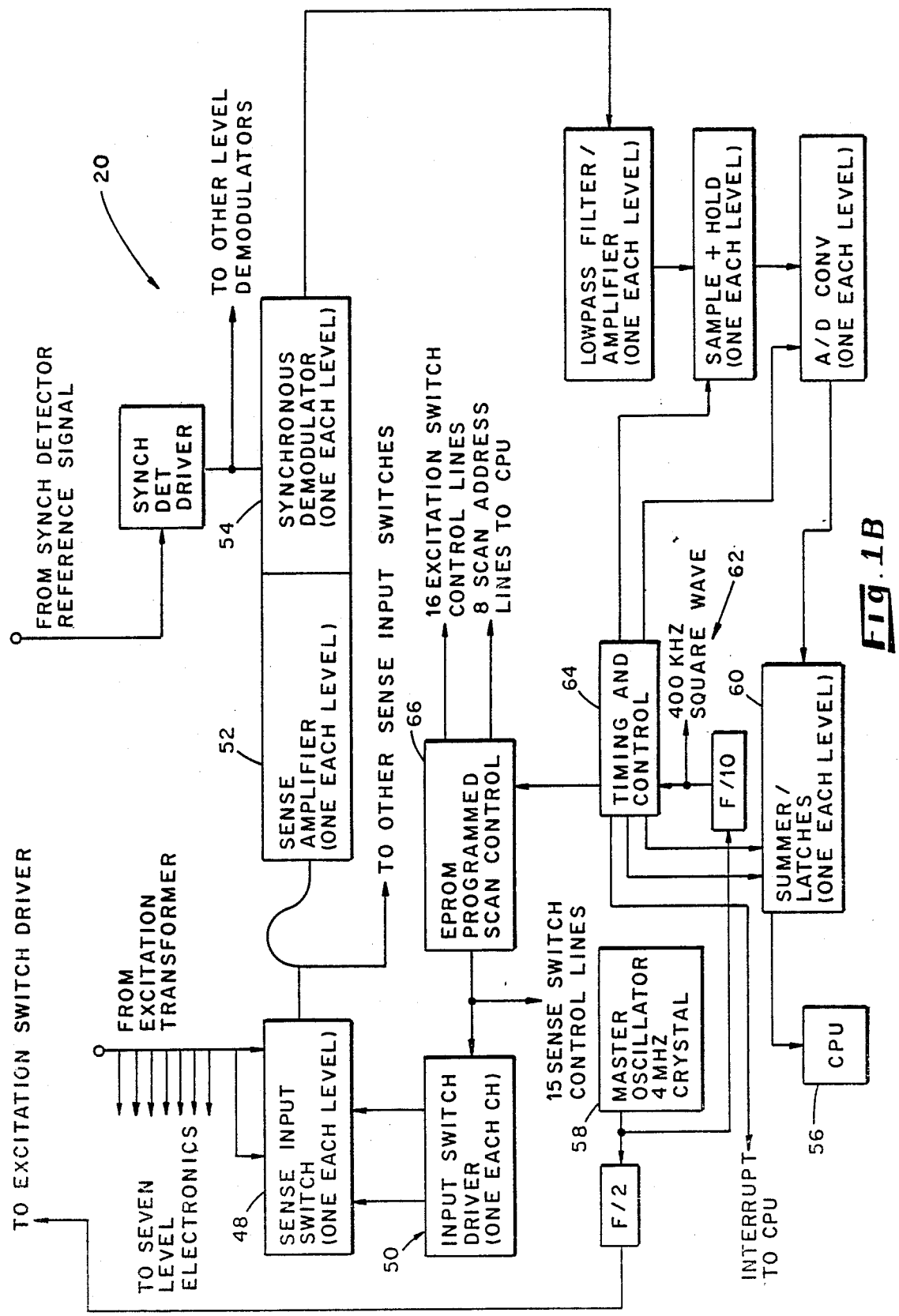

With reference now to the drawings in which like numerals represent like elements, a block diagram of a capacitance imaging system 20 is shown in FIGS. 1A and 1B. In FIG. 1A, a schematic cross section of a fluidized-bed 22 is shown with 16 circumferential electrodes 24 provided therearound at a plurality of levels as indicated. Electrodes 24 are preferably attached to the inside wall of the fluidized-bed vessel 23 (see FIG. 6). Electrodes 24 are individually excited with either a positive or negative (0°- or 180°-phase) excitation (+E or −E) of 400 kHz sine wave voltage or unexcited and shorted to common by means of excitation transformers 26 and excitation switches 28. The phase and on/off excitation state for each of the sixteen electrodes 24 is controlled by excitation switches 28. The switching arrangement is defined by a control code which allows electrodes 24 to be independently excited with a 0°- or 180°-phase sine wave voltage or unexcited (zero voltage).

Figure 2:
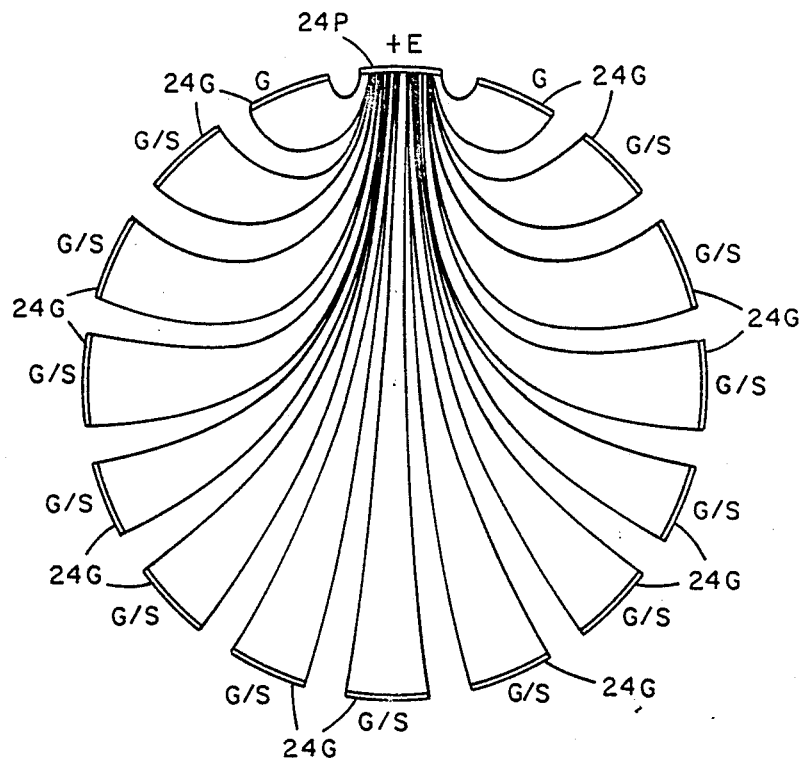
FIGS. 2-5 are schematic representations of different field patterns which can be generated using the capacitance imaging system of the present invention.
Figure 3:
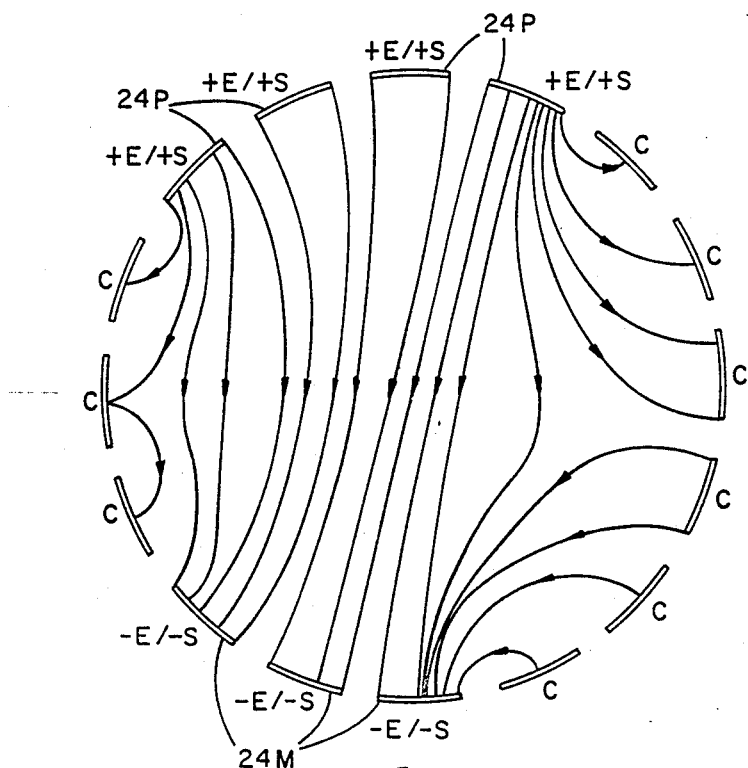
Figure 4:
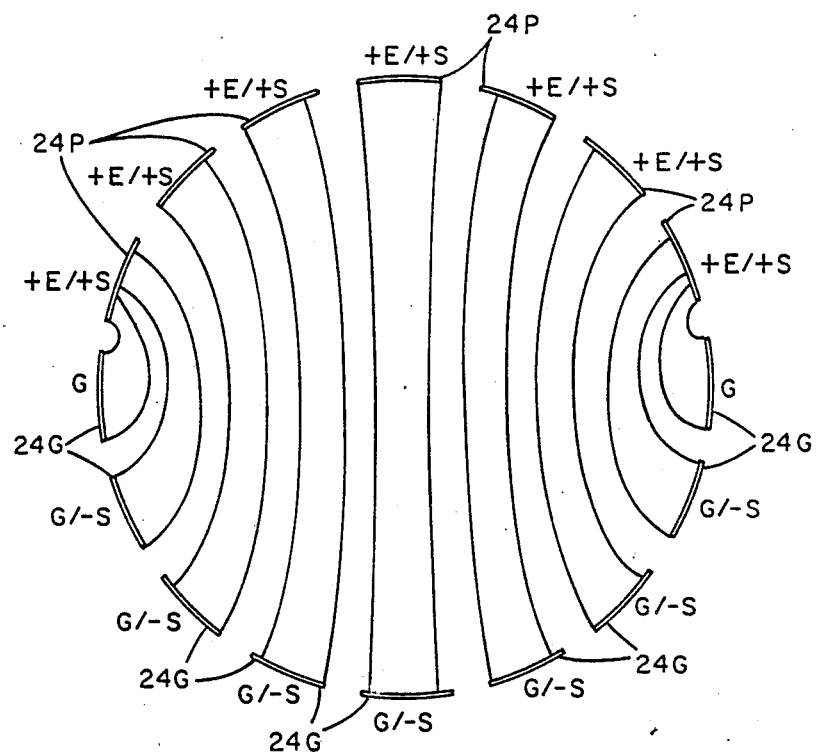
Figure 5:
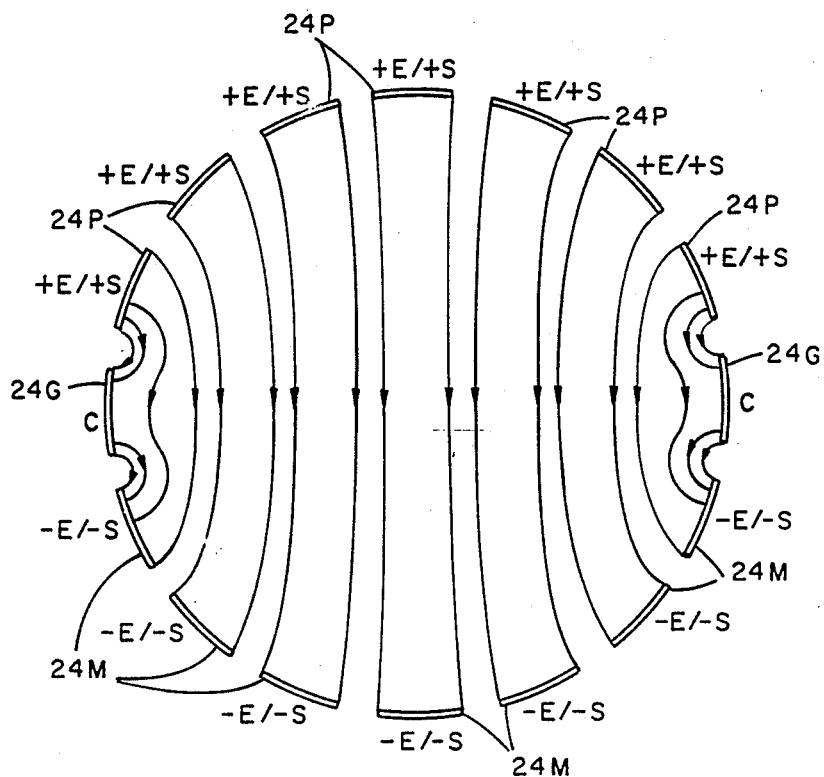

With capacitance imaging system 20 described above, it should be apparent that many different current flux field pattersn can be created in fluidized-bed 22. Schematic depictions of four of these current flux field patterns are provided in FIGS. 2–5. In particular, FIG. 2 shows one electrode 24P at +E (0°-phase) and all other electrodes 24G at zero voltage (ground or common voltage). The pattern depicted in FIG. 3 is for four electrodes 24P at +E and three electrodes 24M at −E, while all of the other electrodes 24G are at ground potential. Seven electrodes 24B are at +E and nine electrodes 24G are grounded in the current flux field pattern depicted in FIG. 4. A symmetrical field results when seven electrodes 24P are at +E and seven electrodes 24M are at −E and two electrodes 24G are at ground as shown in FIG. 5.

It should be appreciated that the current flux field patterns depicted in FIGS. 2–5 are just a few of the many possible field patterns which can be generated wit the presented invention. In addition, all of these field patterns can be rotated through 360° in 22.5° steps with appropriate switching using the sixteen electrodes 24 depicted. The importance of the current flux patterns is in delineating the boundaries of the capacitance measurements.

With capacitance imaging system 10, the excitation level of each electrode 24 can be set at up to 200 volts p-p. This excitation level is maintained by an excitation control of 30 using a feedback level signal from an excitation level detector 32 and applying it to a 400 kHz voltage-controlled-gain amplifier 34.

Figure 6:
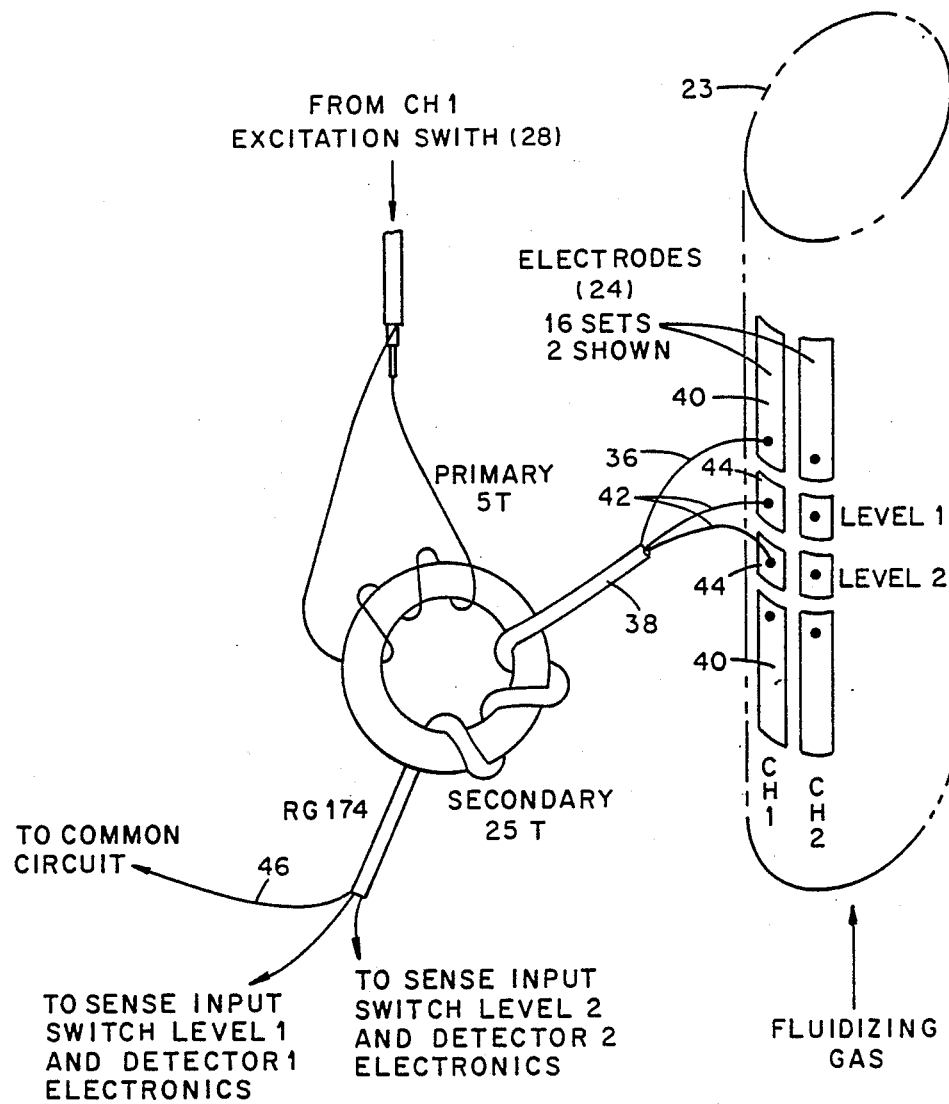
FIG. 6 is a schematic representation of an excitation transformer and associated electrodes according to the present invention.

A more detailed drawing of an excitation transformer 26 is presented in FIG. 6. A high end 36 of a transformer secondary winding shield 38 is connected to the guard (end) electrodes 40. Winding conductors 42 (only two are shown) are connected to levels 1 and 2 sense electrodes 44 (of course, a full system as contemplated would have eight such levels and hence channels of eight electrodes 44 and associated winding conductors 42). Low end 46 of excitation secondary winding shield 38 connects to a circuit common as indicated. Winding conductors 42 then connect to sense input switches 48 for levels 1 through 8 (in a full system) such as the input switching circuits depicted in FIG. 1B.

A sense amplifier 52 is connected to the output of a sense switch 48 for each level. The amplified capacitance signal from sense amplifier 52 is then detected by a synchronous demodulator 54. The detected signal is then further amplified, filtered, sampled, and converted to digital form for computer processing by a CPU 56 as indicated.

All functions of capacitance imaging system 20 are made phase coherent to a master 4 MHz crystal clock 58 to preclude nonstationary variations in circuit signals. Clock 58 is divided by 10 in divider 60 to provide a 400 kHz sub-clock reference 62 for the excitation source input and for timing and control 64. A 2 MHz square wave is also derived from master clock 58 to supply a square wave bias voltage for excitation switches 28.

Data acquisition (sample and conversion) and scan timing are based upon a 400 kHz sub-clock frequency. Up to 10 analog-to-digital conversions are performed at 2.5 microsecond intervals and averaged for each measurement to enhance signal to noise. The maximum scan rate of 25,000 measurements per second is obtained by frequency division of the 400 kHz by sixteen. This or other slower rates can be selected by jumpers. The upper scan rate is limited by the excitation frequency and detection circuitry response.

Scan control is defined by the control word coding stored in the EPROM programmed scan control 66.

Using an EPROM 66 allows the maximum possible scan flexibility for selection of electrodes 24 for +E or −E and + sensing or − sensing. As EPROMs 66 are sequenced through their range of addresses, a serial stream of up to 256 programmed control codes are generated that operate excitation switches 28 and sense switches 48 to provide a set of up to 256 desired capacitance measurements in bed 22. The set of measurements is repeated 100 times per second.

Each set of measurements which takes up to 256×40 microseconds (or about 10 milliseconds) is transformed into a two-dimensional density map for the cross section at each level. By combining the two-dimensional maps at the eight elevation levels, a three-dimensional density map is obtained. It should be appreciated that for each of the seven additional levels, some of the electronics shown in FIG. 1B such as the sense input switch, sense amplifier, synchronous demodulator, low pass filter/amplifier, sample and hold, A/D converter, summers/latches, and sense input switch driver must be duplicated. Also, because of the massive data processing and high rates, a fast micro-computer is required at each level (eight total for this embodiment) to transform the measurements from each level into a real three-dimensional density map.

Figure 7A:
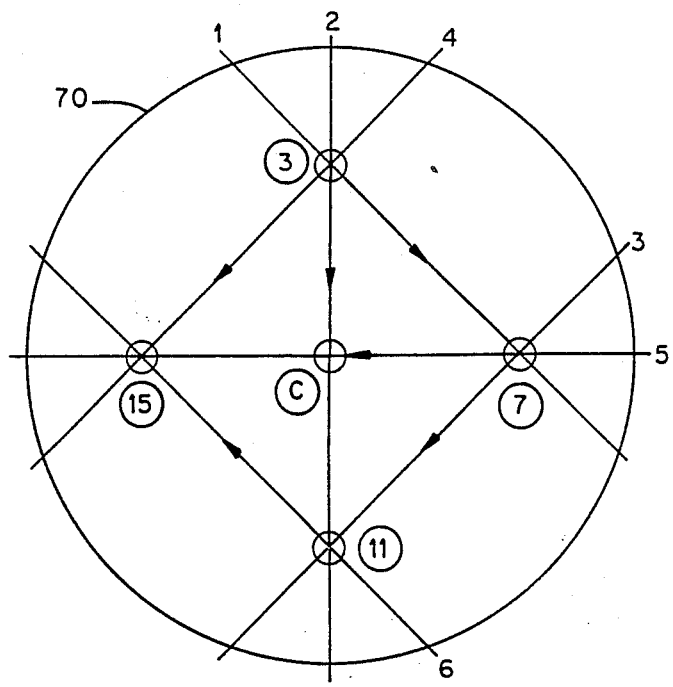
FIG. 7A is a schematic representation of a level in a bed showing the position of voids experimentally used during testing of the present invention.

The present invention has been tried experimentally. An experimental static test bed was constructed of plastic pipe which was 6 inches in diameter and 30 inches long. Sixteen equally spaced stainless steel metal plate electrodes were fastened to the inside surface of the pipe. Measurements were then made of capacitance across a bed through six different paths which are shown numbered 1–6 on the outside of a bed cross section 70 as shown in FIG. 7A. The bed consisted of sand granules and a void was created in the bed using a 2⅜ inch diameter, thin-walled plastic bottle at different locations. For each void location, a set of six measurements were taken from excited pairs of the sixteen electrodes with all other electrodes grounded.

Figure 7B:
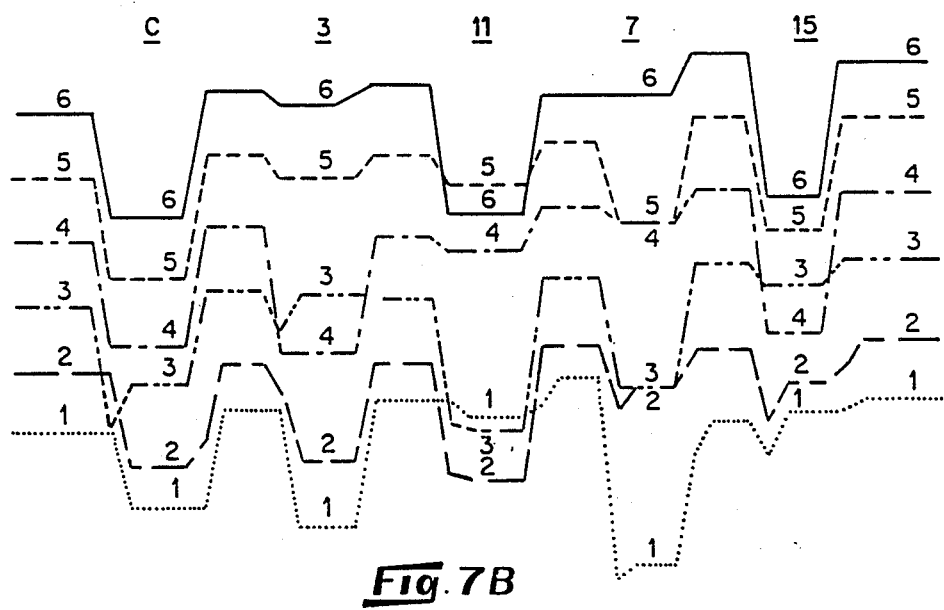
FIG. 7B is a two-dimensional response of the voids in the bed depicted in FIG. 7A.

A plot of the six measurements is provided in FIG. 7B. The plot is the deviations from a no-void condition for the void placed at the five locations. These five locations are (center 3, 11, 7 and 15). The void was removed between measurement sets to reestablish no-void base lines. The excitation used was 125 volts p-p, 400 kHz sine wave, a six second scan rate, and 50 sets.

It can be seen in FIG. 7B that for any measurement path that intersects the void, a negative (lowered capacitance) deviation results. Thus, when the void is placed at location 3, paths 1, 2 and 4 displayed a significant negative change while paths 3, 5, and 6 changed only slightly.

Using the data from a set of six measurements, the relative densities ($D_c$, $D_3$, $D_7$, $D_{11}$, $D_{15}$) at five pixel locations (c, 3, 7, 11 and 15) are estimated using the following equations:

$$M_1 = D_3\, D_7$$

$$M_2 = D_3\, D_c\, D_{11}$$

$$M_3 = D_7\, D_{11}$$

$$M_4 = D_3\, D_{15}$$

$$M_5 = D_7\, D_c\, D_{15}$$

$$M_6 = D_{11}\, D_{15}$$

From which, $$D_c = \sqrt{(M2\ M5)/(M1\ M6)}$$

$$D3 = \sqrt{(M2\ M1)/(M3\ D_c)}$$

$$D7 = M1/D3$$

$$D11 = M3/D7 = M2/(D3\ D_c)$$

$$D15 = M4/D3 = M6/D11$$

where M1 through M6 are the standardized capacitance measurements obtained along paths 1 through 6 as shown in FIG. 7A. The measurements are standardized by collecting calibration data for two different known and uniform bed media over the six paths and finding the relative measurement sensitivities for the six paths. Standard bed media are air and seven-hundred micron uniform-sized plastic spheres. M1 through M6 are standardized by dividing their relative measurement sensitivies for paths 1 through 6, respectively.

It should be appreciated that the present invention provides a capacitance method for obtaining a three-dimensional map of the density within a dynamic fluidized bed at rates of 100 maps per second. The present system also allows a switching arrangement employing excitation transformers with shielded multi-turn secondary windings for multi-level measurements.

It should also be appreciated that the means of excitating the electrodes with +E (0°-phase) or −E (180°-phase) or shorting electrodes to common allows the system of the present invention to provide a symmetrical or non-symmetrical field as desired.

It should further be appreciated that the present invention provides a means of switch selecting the sense electrode pairs from which the measurements are made. This includes a + sense and a − sense switch to allow measurement of capacitance current that links any two different electrode combinations while selecting any electrode excitation combination.

The use of a programmed EPROM also allows the generation of a sequence of up to 256 control codes at 25,000 codes per second for controlling the +E, −E, + sense and − sense switches to perform 25,000 measurements per second at each elevation level. Therefore, for eight levels, 200,000 measurements per second are made.

It should still further be appreciated that the use of a transformer-coupled 2 MHz bias allows the use of metal oxide field effect transistors (MOSFETS) used in isolated, high-speed (5 microseconds operate time), high-voltage, solid-state switches for the excitation switching.

A means of exciting any combination of electrodes with +E and the remaining electrodes with −E or no excitation (shorted to common) is further provided.

While the present invention has been described with respect to an exemplary embodiment thereof, it will be understood by those of ordinary skill in the art that variations and modifications can be effected within the scope and spirit of the invention.

I claim:

1. An apparatus for providing a three-dimensional capacitance density imaging of a gasified bed in a longitudinally extending containment vessel comprising:
   a plurality of electrodes circumferentially spaced apart from one another about the bed in each of a plurality of longitudinally spaced apart levels along a longitudinal length of the bed;
   excitation means for individually and selectively exciting said electrodes at each of said levels independently of the other levels to generate a plurality of current flux field patterns in the bed at each level;
   sensing means for sensing the current flux patterns at each level;
   determining means for determining a two-dimensional density pattern of the bed at each level from the sensed current flux patterns; and
   combining means for combining the determined two-dimensional density patterns at each level to provide a three-dimensional density image of the bed over the longitudinal length thereof encompassed by the electrodes.

2. An apparatus for providing a density map as claimed in claim 1 wherein said excitation means excites said electrodes with one of a positive 0°-phase voltage, a negative 180°-phase voltage, and a zero voltage.

3. An apparatus for providing a density map as claimed in claim 2 wherein said excitation means generates symmetrical current field patterns at each level.

4. An apparatus for providing a density map as claimed in claim 2 wherein said excitation means generates non-symmetrical current field patterns.

5. An apparatus for providing a density map as claimed in claim 2 wherein such electrode is in a channel, wherein said excitation means includes an excitation transformer for each electrode channel.

6. An apparatus for providing a density map as claimed in claim 5 wherein each said excitation transformer includes a shielded multi-turn secondary winding for each said electrode in the associated channel.

7. An apparatus for providing a density map as claimed in claim 6 wherein said electrodes in each channel include a sense electrode at each level and guard electrodes at each end of the channel which are connected to a secondary winding shield of said excitation transformer means.

8. An apparatus for providing a density map as claimed in claim 1 wherein said excitation means includes a means for maintaining the electrical excitation at a predetermined voltage.

9. An apparatus for providing a density map as claimed in claim 1 and further including a clock means for generating a reference signal for said excitation means, said sensing means, and said determining means.

10. An apparatus for providing a density map as claimed in claim 1 wherein said sensing means includes a switch means for allowing the sensing of capacitance current at any two different electrode combinations at anyone of said plurality of levels.

11. A method for generating a three-dimensional capacitance density image of a gasified bed in a longitudinally extending containment vessel comprising the steps of:
   providing a plurality of electrodes at circumferentially spaced apart locations about the bed in each of a plurality of longitudinally spaced apart levels along a longitudinal length of the bed in channels;
   generating a plurality of current flux field patterns in the bed at each level independently of each other level by electrically exciting selected electrodes in each level;
   sensing the current flux patterns generated at each level;

determining the two-dimensional density of the bed at each level from the sensed current flux patterns; and combining the determined two-dimensional density patterns at each level provide a three-dimensional density image of the bed along the longitudinal length thereof encompassed by the electrodes.

12. A method for generating a density map as claimed in claim 11 wherein said generating step includes the step of exciting the electrodes with one of a positive 0°-phase voltage, a negative 180°-phase voltage and a zero voltage.

13. A method for generating a density map as claimed in claim 11 and further including the step of generating a reference clock signal for synchronously timing and controlling said sensing, determining and combining steps.

* * * * *